US006342493B1

United States Patent
Onodera et al.

(10) Patent No.: US 6,342,493 B1
(45) Date of Patent: Jan. 29, 2002

(54) CRYSTALLOGRAPHICALLY STABLE AMORPHOUS CEPHALOSPORIN COMPOSITIONS AND PROCESS FOR PRODUCING THE SAME

(75) Inventors: Masahiro Onodera; Masamichi Sukegawa; Kiyoshi Yasui; Tatsuo Watanabe; Toyomi Sato; Yasushi Murai; Katsuharu Iinuma, all of Odawara (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 0 days.

(21) Appl. No.: 09/582,937
(22) PCT Filed: Jan. 7, 1999
(86) PCT No.: PCT/JP99/00020
  § 371 Date: Jul. 7, 2000
  § 102(e) Date: Jul. 7, 2000
(87) PCT Pub. No.: WO99/34832
  PCT Pub. Date: Jul. 15, 1999

(30) Foreign Application Priority Data

Jan. 7, 1998 (JP) .......................................... 10-001920

(51) Int. Cl.[7] .............................................. A61K 31/545
(52) U.S. Cl. ...................... 514/200; 514/202; 514/208; 514/960
(58) Field of Search ................................ 514/200, 202, 514/208, 960

(56) References Cited

U.S. PATENT DOCUMENTS 6,294,669 B1 * 9/2001 Yasui et al. .................. 540/227

* cited by examiner

Primary Examiner—Frederick Krass
Assistant Examiner—Donna Jagoe
(74) Attorney, Agent, or Firm—Larson & Taylor PLC (57) ABSTRACT

Processes are provided for the preparation of orally administrable, yellow and powdery compositions essentially consisting of particles composed of a homogeneous mixture of an amorphous Cefditoren pivoxil substance with a water soluble high-molecular additive. These compositions can be produced by dissolving crystalline Cefditoren pivoxil substance and the water-soluble high-molecular additive in an aqueous solution of an acid, then neutralizing the resultant solution, to co-precipitate the product, and drying the thus precipitated product, followed by recovering the product in the form of the above-mentioned particles.

7 Claims, 3 Drawing Sheets

CRYSTALLOGRAPHICALLY STABLE AMORPHOUS CEPHALOSPORIN COMPOSITIONS AND PROCESS FOR PRODUCING THE SAME

TECHNICAL FIELD

This invention relates to an orally administrable and powdery composition consisting essentially of a number of particles each comprising a crystallographically stable and amorphous cephalosporin. More specifically, this invention relates to a novel, orally administrable and powdery composition consisting essentially of particles which each have a uniform internal texture within each particle and each are formed from a homogeneous mixture of an amorphous and water-soluble substance of 7-[(Z)-2-(2-aminothiazol-4-yl)-2-methoxyiminoacetamido]-3-[(Z)-2-(4-methylthiazol-5-yl) ethenyl]-3-cephem-4-carboxylic acid pivaloyloxymethyl ester, that is, Cefditoren pivoxil (a generic name), with a water-soluble, high-molecular additive, for example, a water-solubilized derivative of cellulose. This invention further relates to processes for the preparation of the novel, orally administrable and powdery composition as above-mentioned.

BACKGROUND ART

The cephem compound known under the generic name "Cefditoren" is the compound which is represented by the following formula (A)

(A)

and which compound was at first named as 7-[2-methoxyimino-2-(2-aminothiazol-4-yl)acetamido]-3-[2-(4-methylthiazol-5-yl)vinyl]-3-cephem-4-carboxylic acid (syn-isomer, cis-isomer) (refer to Japanese Patent Publication Hei 3-64503 specification, U.S. Pat. No.4,839,350 and European Patent No.0175610 specification).

Cefditoren pivaloyloxymethyl ester is a pro-drug known under the generic name "Cefditoren pivoxil" and is the compound represented by the following formula (B)

(B)

Cefditoren pivoxil is also known in the name of "(−)-(6R, 7R) -7-[(Z)-2-(2-aminothiazol-4-yl)-2-methoxyiminoacetamido]-3-[(Z)-2-(4-methylthiazol-5-yl) ethenyl]-8-oxo-5-thia-1-azabicyclo[4.2.0]oct-2-ene-2-carboxylic acid 2,2-dimethylpropionyloxymethyl ester" and is described on page 317 of the literature "Merck Index", the 12th Edition to be a pale yellow-colored powdery substance-melting at 127~129° C. Another chemical name of the compound "Cefditoren pivoxil" is 7-[(Z)-2-(2-aminothiazol-4-yl)-2-methoxyiminoacetamido]-3-[(Z)-2-(4-methylthiazol-5-yl)ethenyl]-3-cephem-4-carboxylic acid pivaloyloxymethyl ester.

Cefditoren pivoxil, when orally administered, can be well absorbed by the digestive tracts, within which Cefditoren pivoxil is hydrolyzed into Cefditoren. It is known that Cefditoren is an antibiotic substance possessing an extremely broad antibacterial spectrum but a low toxicity and Cefditoren is very excellently useful for the therapeutic treatment and prevention of diseases which are caused by gram-positive and gram-negative bacteria. At present, Cefditoren pivoxil is widely utilized as an orally administrable pro-drug for the therapy.

We, the present inventors, had made investigations with the intention of obtaining a highly pure product of Cefditoren pivoxil, and as a result, we already succeeded in obtaining Cefditoren pivoxil in the form of an orthorhombic crystalline substance (at a purity of: 97~98%) of a melting point of 206~215.7° C. (with decomposition), by adopting a certain particular process (refer to International Open-Laying Publication No. WO98/12200 of PCT application No. PCT/JP97/03340, issued on Mar. 26, 1998). This orthorhombic crystalline substance of Cefditoren pivoxil shows such advantages that it has a high purity, a high thermal stability and a high storage-stability under high-humidity conditions, but still it shows such disadvantage that it itself is not so suitable for the purpose of oral administrations due to its poor solubility in water.

DISCLOSURE OF INVENTION

In general, for such medicinal compounds which are sparingly soluble in water, it is well known that the solubility or the dissolution speed of the sparingly water-soluble compounds in water can exert a great influence on the absorption in vivo of said compounds. Thus, many reports were presented on how to improve the water-solubility of such medicinal compounds which are sparingly soluble in water. One of the reported proposals is a method in which a medicinal compound sparingly soluble in water is converted into an amorphous substance, thus to improve the solubility of the compound in water. It is known that an amorphous substance generally has a higher solubility in water, as compared with that of the corresponding crystalline substance. It is therefore expectable that if the orthorhombic crystalline substance of Cefditoren pivoxil sparingly soluble in water is converted into an amorphous substance which is; of a higher solubility in water, there may be afforded such a water-soluble and highly pure product of Cefditoren pivoxil which is capable of exhibiting its therapeutic efficacy to a full extent.

We have therefore further prosecuted diligently our investigations in order to solve the problem of converting the crystalline Cefditoren pivoxil into an amorphous substance having a higher water-solubility. As a result, we have now found that there can successfully be prepared an orally administrable, yellow-colored powdery composition consisting essentially of such particles which each have a uniform internal texture or tissue within each particle and which each are formed from a homogeneous mixture of the amorphous Cefditoren pivoxil substance having a high water-solubility and a high thermal stability, with a water-soluble high-molecular additive, when use is made of such a process which comprises dissolving a crystalline Cefditoren pivoxil in an acidic aqueous solution containing a water-soluble high-molecular additive, for example, a water-solubilized derivative of cellulose and an acid dissolved therein, thereby to form an acidic aqueous solution containing Cefditoren pivoxil, the water-soluble high-molecular additive and the acid dissolved therein, then slowly adding to the resultant acidic aqueous solution an aqueous solution of an inorganic base to neutralize said acidic aqueous solution to a neutral or a substantially neutral pH value, with co-precipitating Cefditoren pivoxil and said water-soluble high-molecular additive simultaneously from said aqueous solution during the neutralization operation, then washing the deposited precipitate with an aqueous solution of the water-soluble high-molecular additive, drying the washed precipitate, and recovering the resulting particulate product so dried. This invention has been established on the basis of these findings mentioned above.

Thus, according to a first aspect of this invention, there is provided an orally administrable, yellow-colored powdery composition consisting essentially of solid particles which each are formed of a homogeneous mixture of a crystallographically stable, amorphous and water-soluble substance of Cefditoren pivoxil with a water-soluble high-molecular additive, and which particles have a uniform, internal texture within each particle, characterized in that said yellow-colored powdery composition consists essentially of the solid particles each formed of the homogeneous mixture of (i) the crystallographically stable, amorphous and water-soluble substance of Cefditoren pivoxil, namely 7-[(Z)-2-(2-aminothiazol-4-yl)-2-methoxyiminoacetamido]-3-[(z)-2-(4-methylthiazol-5-yl)ethenyl]-3-cephem-4-carboxylic acid pivaloyloxymethyl ester, with (ii) the water-soluble high-molecular additive which is either such a pharmaceutically acceptable, water-solubilized derivative of cellulose as chosen from hydroxypropylmethyl cellulose, hydroxypropylmethyl cellulose phthalate, hydroxypropyl cellulose, methyl cellulose and a pharmaceutically acceptable alkali metal salt or alkaline earth metal salt of carboxymethyl cellulose, or pluran, carrageenan, polyvinylpyrrolidone or an alginic acid ester of polypropylene glycol, that the water-soluble high-molecular additive (ii) contained in the above-mentioned solid particles is present in said particles in a proportion of 0.5%~5% based on the weight of the Cefditoren pivoxil substance, that said particles fuse at a temperature of 120° C. or higher, but do not show any definite melting point, that the amorphous substance of Cefditoren pivoxil (i) contained in said particles does not show any peak of the angle of diffraction in a X-ray powder diffractometry chart of said particles but exhibits in its infrared absorption spectrum (as measured by pelleted potassium bromide method) a substantially broader peak of absorption at a wave number of 1750 $cm^{-1}$, as compared with the sharp peak of absorption exhibited by the orthorhombic crystalline substance of Cefditoren pivoxil at a wave number of 1750 $cm^{-1}$ in the infrared absorption spectrum, and that the amorphous substance of Cefditoren pivoxil (i) contained in said particles can be dissolved in an acidified water containing hydrochloric acid (pH 1.2) at a solubility of at least 4 mg/ml of Cefditoren pivoxil at 37° C. and has a crystallographical stability such that said amorphous Cefditoren pivoxil substance does not involve crystallization when stored at 40° C. for 4 months in a sealed container under dry conditions.

One preferred example of the powdery composition according to the first aspect of this invention is such a composition consisting essentially of particles each formed of a homogeneous mixture of a crystallographically stable, amorphous and water-soluble substance of Cefditoren pivoxil with the water-soluble high-molecular additive which is hydroxypropylmethyl cellulose, hydroxypropyl cellulose, methyl cellulose or polyvinylpyrrolidone, and which additive as blended is present in a proportion of 1%~3% based on the weight of the Cefditoren pivoxil.

Further, in respect of the respective solid particles which each are formed of the homogeneous mixture of the amorphous Cefditoren pivoxil with the water-soluble high-molecular additive and which are present in the powdery composition according to the first aspect of this invention, we have now observed, under a polarizing microscope of 400 magnifications or under an electron microscope, the surface texture or tissue of said solid particles, and we have found that the surface of each particle has a simple and uniform texture or tissue. We cannot find any presence of independent and separate grains of either Cefditoren pivoxil or the high-molecular additive in the surface of each particle.

In the powdery composition according to the first aspect of this invention, the water-soluble high-molecular additive which is to be mixed with the amorphous Cefditoren pivoxil, and which is the water-solubilized cellulose derivatives, or pluran, carrageenan, polyvinylpyrrolidone or an arginic acid ester of polypropylene glycol, may be of a grade thereof which usually is used and incorporated in the formulations of medicines as a binder or a suspending agent. Among the water-soluble high-molecular additives to be usable in the composition of the first aspect of this invention, the water-solubilized derivatives of cellulose are particularly preferred. As the water-solubilized derivatives of cellulose, there may be used hydroxypropylmethyl cellulose (abbreviated as HPMC), hydroxypropylmethyl cellulose phthalate (abbreviated as HPMCP), hydroxypropyl cellulose (abbreviated as HPC), methyl cellulose (abbreviated as MC), carboxymethyl cellulose calcium salt or carboxymethyl cellulose sodium salt. The use of hydroxypropylmethyl cellulose (HPMC), hydroxypropyl cellulose (HPC) or methyl cellulose (MC) is particularly preferred.

In the homogeneous mixture which constitutes the solid particles present in the powdery composition of the first aspect of this invention, and which is composed of the amorphous Cefditoren pivoxil and the water-soluble high-molecular additive, the proportion of the water-soluble high-molecular additive to be incorporated therein may be in a range of 0.5%~5% , preferably in a range of 1%~3% based on the weight of Cefditoren pivoxil.

Further, we have tried to measure the melting point of the solid particles present in the composition of the first aspect of this invention, by placing the particles in a melting point-measuring apparatus. As a result, we have found that these solid particles fuse at 120~150° C. with decomposition, but do not show any one definite melting point.

We have further carried out the measurement of powder X-ray diffraction of the solid particles present in the composition of the first aspect of this invention, by placing the particles in a X-ray powder diffraction apparatus (Rigaku Denki K. K.: Geigerflex 2027). Upon analysis of the pattern of the resulting X-ray diffraction chart of said X-ray powder diffraction, it is shown that no peak is appearing in the angle of diffraction, indicating that the Cefditoren pivoxil substance existing in said solid particles is amorphous in nature.

We have further carried out a measurement of infrared absorption spectrum of the solid particles present in the composition of the first aspect of this invention, by mixing the solid particles with an amount of potassium bromide, compressing the resultant mixture to pelletize the same, and then placing the resulting pellet into an infrared absorption spectrometer. In the spectrum chart thus obtained, the infrared absorption spectrum of the Cefditoren pivoxil substance present in said powder exhibits at a wave number of 1750 cm$^{-1}$ an absorption peak which is substantially broader than such a sharp absorption peak that the orthorhombic crystalline substance of Cefditoren pivoxil exhibits at a wave number of 1750 cm$^{-1}$ in its infrared absorption spectrum.

We have also made a measurement of powder X-ray diffraction of the previously stored solid particles present in the composition of the first aspect of this invention, by placing and storing said solid particles in a sealed container under a dry air atmosphere at 40° C. for 4 months, followed by measuring the powder X-ray diffraction of the stored particles in the powder X-ray diffraction apparatus used as above. Analysis of the pattern of the resulting powder X-ray diffraction chart did not indicate any peak in the angle of diffraction in the chart. Thus, it is demonstrated that the Cefditoren pivoxil present in the particles stored as above has remained in the amorphous state and that it is crystallographically stable and can maintain the amorphous state even after the storage thereof for a long period of time.

We presume that in the composition of this invention, the water-soluble high-molecular additive co-existent in admixture with the Cefditoren pivoxil in the solid particles can possess a function capable of inhibiting the molecules of Cefditoren pivoxil from undergoing their crystallization.

The solid particles present in the composition of this invention have an average particle diameter within the range of 0.5 $\mu$~100 $\mu$.

The solid particles present in the composition of this invention were tested for the measurement of their water-solubility as shown in Test Example given hereinafter. It was thus found that the amorphous Cefditoren pivoxil contained in said particles was soluble in an acidified water of pH 1.2 containing about 0.1 N hydrochloric acid (corresponding to the artificial gastric juice specified in Japanese Pharmacopedia) and had a solubility of at least 4 mg/ml in the acidified water at 37° C.

Furthermore, we have proceeded our further investigation. Thus, when we carry out, for the purpose of producing the particles of the powdery composition of the first aspect invention, the process which comprises the steps of completely dissolving a crystalline Cefditoren pivoxil in an acidic aqueous solution containing and having dissolved therein a water-soluble high-molecular additive and an acid, thereby to prepare an acidic aqueous solution containing Cefditoren pivoxil, the water-soluble high-molecular additive and the acid all dissolved therein, then slowly adding to the resulting acidic aqueous solution so prepared an aqueous solution of an inorganic base, thereby to neutralize the acidic aqueous solution to a neutral pH value or a substantially neutral pH value, allowing, during the neutralization operation, Cefditoren pivoxil and the first-mentioned water-soluble high-molecular additive to co-precipitate simultaneously from said aqueous acidic solution, separating and then washing the deposited precipitate with an aqueous solution of the first-mentioned a water-soluble high-molecular additive and subsequently drying the washed precipitate, we have now found that the aforesaid process can be carried out in such one modified manner that the first mentioned water-soluble high-molecular additive, which was contained in said acidic aqueous solution of the water-soluble high-molecular additive and the acid to be employed for the dissolution of Cefditoren pivoxil, and which is to be contained in the washing aqueous solution of the high-molecular additive for washing the deposited precipitate, is replaced by such a second, water-soluble high-molecular additive which is made of a compound different from said first-mentioned high-molecular additive, when it is intended to prepare a washing aqueous solution of the water-soluble high-molecular additive which is to be employed in the step of washing said deposited precipitate therewith, and thereby at least a portion of the second, water-soluble high-molecular additive present in so prepared the washing aqueous solution of the second additive as employed for the aforesaid washing step is allowed to transfer into the surface of the precipitate particles during said washing step. It has further been found that, when said washing step is conducted with said aqueous solution of the second-mentioned additive, followed by conducting the steps of recovering and drying the precipitate particles of which the surface have contained therein the second, water-soluble high-molecular additive as transferred from the washing aqueous solution employed in said washing step, there can be afforded such dried precipitate particles wherein the surface layer of each of said solid particles as collected is formed from a homogeneous mixture of the amorphous Cefditoren pivoxil with the first, water-soluble high-molecular additive and the second, water-soluble high-molecular additive, but wherein the central portion or core portion of each of the solid particles lying under the surface layer of the solid particles is formed from a homogeneous mixture of the amorphous cefditoren pivoxil with the first, water-soluble high-molecular additive.

According to a second aspect of this invention, therefore, there is provided an orally administrable, yellow-colored powdery composition consisting essentially of particles which each substantially comprise mixtures of a crystallographically stable, amorphous and water-soluble substance of Cefditoren pivoxil with water-soluble high-molecular additive or additives, and which particles have a uniform, internal texture within each particle, characterized in that the yellow-colored powdery composition consists essentially of the particles each substantially comprising a mixture of (i) the crystallographically stable, amorphous and water-soluble substance of Cefditoren pivoxil, namely 7-[(Z)-2-(2-aminothiazol-4-yl)-2-methoxyiminoacetamido]-3-[(Z)-2-(4-methylthiazol-5-yl)ethenyl]-3-cephem-4-carboxylic acid pivaloyloxymethyl ester, with (ii) a first, water-soluble high-molecular additive which is either such a pharmaceutically acceptable, water-solubilized derivative of cellulose as chosen from hydroxypropylmethyl cellulose, hydroxypropylmethyl cellulose phthalate, hydroxypropyl cellulose, methyl cellulose and a pharmaceutically acceptable alkali metal salt or alkaline earth metal salt of carboxymethyl cellulose, or pluran, carrageenan, polyvinylpyrrolidone or an alginic acid ester of polypropylene glycol, that the central portion or core portion of the respective particles which is lying under the surface layer of said respective particles is formed only from a homogeneous mixture of (i) the amorphous substance of Cefditoren pivoxil with (ii) the above-mentioned first, water-soluble high-molecular additive, but the surface layer of said particles is formed from a homogeneous mixture of (i) the amorphous substance of Cefditoren pivoxil with (ii) the first, water-soluble high-molecular additive and also with (iii) such a second, water-soluble high-molecular additive which is additionally incorporated and which second additive is made of a substance different from the above-mentioned first, water-soluble high-molecular additive present just in the central portion or core portion of said particles lying under said surface layer of the particle, and which second, water-soluble high-molecular additive is selected from hydroxypropylmethyl cellulose, hydroxypropyl cellulose, methyl cellulose and polyvinylpyrrolidone, that both the first, water-soluble high-molecular additive (ii) and the second, water-soluble high-molecular additive (iii) are present in a total proportion of them of 0.5%~5% based on the weight of the Cefditoren pivoxil substance contained in said particles, that said particles fuse at a temperature of 120° C. or higher, but do not show any definite melting point, that the amorphous substance of Cefditoren pivoxil (i) contained in said particles does not show any peak of the angle of diffraction in a powder X-ray diffractometry chart of said particles but exhibits in its infrared absorption spectrum (as measured by pelleted potassium bromide method) a substantially broader peak of absorption at a wave number of 1750 $cm^{-1}$, as compared with the sharp peak of absorption exhibited by the ortho-rhombic crystalline substance of Cefditoren pivoxil at a wave number of 1750 $cm^{-1}$ in the infrared absorption spectrum, and that the amorphous substance of Cefditoren pivoxil (i) contained in said particles can be dissolved in an acidified water containing hydrochloric acid (pH 1.2) at a solubility of at least 4 mg/ml of Cefditoren pivoxil at 37° C. and has a crystallographical stability such that said amorphous Cefditoren pivoxil substance does not involve crystallization when stored at 40° C. for 4 months in a sealed container under dry conditions.

A first preferred example of the powdery composition according to the second aspect of this invention is such a composition, wherein the central portion or core portion of the particles constituting the composition, which is lying under the surface layer of the particles, is formed from a homogeneous mixture of the amorphous substance of Cefditoren pivoxil with hydroxypropylmethyl cellulose, but the surface layer of said particles is formed from a homogeneous mixture of the amorphous substance of Cefditoren pivoxil with hydroxypropylmethyl cellulose and also with hydroxypropyl cellulose or methyl cellulose.

A second preferred example of the powdery composition according to the second aspect of this invention is such a composition, wherein the central portion or core portion of the particles constituting the composition, which is lying under the surface layer of the particles, is formed from a homogeneous mixture of the amorphous substance of Cefditoren pivoxil with hydroxypropylmethyl cellulose, but the surface layer of said particles is formed from a homogeneous mixture of the amorphous substance of Cefditoren pivoxil with hydroxypropyl cellulose and also with hydroxypropylmethyl cellulose or methyl cellulose.

A third preferred example of the powdery composition according to the second aspect of this invention is such a composition, wherein the central portion or core portion of the particles constituting the composition, which is lying under the surface layer of the particles, is formed from a homogeneous mixture of the amorphous substance of Cefditoren pivoxil with methyl cellulose, but the surface layer of said particles is formed from a homogeneous mixture of the amorphous substance of Cefditoren pivoxil with methyl cellulose and also with hydroxypropylmethyl cellulose or hydroxypropyl cellulose.

A fourth preferred example of the powdery composition according to the second aspect of this invention is such a composition, wherein the central portion or core portion of the particles constituting the composition, which is lying under the surface layer of the particles, is formed from a homogeneous mixture of the amorphous substance of Cefditoren pivoxil with polyvinylpyrrolidone, but the surface layer of said particles is formed from a homogeneous mixture of the amorphous substance of Cefditoren pivoxil with polyvinylpyrrolidone and also with hydroxypropylmethyl cellulose or hydroxypropyl cellulose or methyl cellulose.

The solid particles present in the composition of the second aspect of this invention have physical and physicochemical properties substantially the same as those of the solid particles present in the composition according to the first aspect of this invention.

Besides, the solid particles present in the composition according to the second aspect of this invention have been found to be such those that, when the surface of the particles are observed under a polarizing microscope or under an electron microscope, said surface has a simple and uniform, internal texture in each particle and does not substantially contain any independently separate grains of Cefditoren pivoxil, nor any independently separate grains of the water-soluble high-molecular additives in the surface texture or tissue of said particles.

Both of the powdery composition according to the first aspect of this invention and the powdery composition according to the second aspect of this invention are orally administrable, and they may be formulated in the form of tablets by blending said composition with excipient(s), for example, starch or talc, and/or binder(s), for example, gelatine or hydroxypropyl cellulose, and a suitable additive agent, and then compressing the resulting blend into tablets. Both of the powdery compositions according to the first and second aspects of this invention may also be formulated in the form of powdery preparations by blending such composition with a pharmaceutically acceptable powdery carrier, for example, starch or cellulose powder.

For a process for the preparation of the powdery composition according to the first aspect of this invention, there is provided, according to a third aspect of this invention, a process for the preparation of a yellow-colored powdery composition consisting essentially of particles which each are formed of a homogeneous mixture of a crystallographically stable, amorphous and water-soluble substance of Cefditoren pivoxil with a water-soluble high-molecular additive, and which particles have a uniform, internal texture within each particle, characterized in that the process comprises a step of dissolving an orthorhombic crystalline substance of Cefditoren pivoxil, namely 7-[(Z)-2-(2-aminothiazol-4-yl)-2-methoxyiminoacetamido]-3-[(Z)-2-(4-methylthiazol-5-yl)ethenyl]-3-cephem-4-carboxylic acid pivaloyloxymethyl ester, in an acidic aqueous solution which is containing a water-soluble high-molecular additive made of either such a water-solubilized derivative of cellulose as chosen from hydroxypropylmethyl cellulose, hydroxypropylmethyl cellulose phthalate, hydroxypropyl cellulose, methyl cellulose and a pharmaceutically acceptable alkali metal salt or alkaline earth metal salt of carboxymethyl cellulose, or pluran, carrageenan, polyvinylpyrrolidone or an alginic acid ester of polypropylene glycol as dissolved at a concentration of 0.05% to 1% (weight/weight basis), and which acidic aqueous solution is containing also hydrochloric acid, phosphoric acid, sulfuric acid, acetic acid, propionic acid or butyric acid at a concentration of 0.1N~12N of the acid, so that the amount of Cefditoren pivoxil dissolved in said acidic aqueous solution is in the range of 10 times to 130 times based on the whole weight of said water-soluble high-molecular additive contained in said acidic aqueous solution, and so that there is prepared an acidic aqueous solution containing Cefditoren pivoxil, the water-soluble high-molecular additive and the acid dissolved therein; a step of subsequently neutralizing the acidic aqueous solution so prepared by adding slowly thereto an aqueous solution or solutions of sodium orpotassium hydroxide, sodium or potassium hydrogen carbonate, or sodium or potassium carbonate, singly or in combination, or an aqueous solution of ammonium hydroxide, with maintaining said acidic aqueous solution at a temperature of 10° C. or below under stirring, and with the amount of the basic sodium or potassium compound or ammonium hydroxide to be added to said acidic aqueous solution being so adjusted that the resulting reaction solution after the neutralization shows a pH value of 6.5~7.1; and a step of continuing during the neutralization reaction the stirring of the aqueous solution containing Cefditoren pivoxil at a temperature of 10° C. or below, to bring about co-precipitation of Cefditoren pivoxil and the water-soluble high-molecular additive simultaneously from the aqueous solution; a step of collecting by filtration or centrifugation, the so deposited precipitate from the resulting neutralization reaction mixture; a step of washing the collected precipitate with an aqueous solution of a water-soluble high-molecular additive made of the same substance as that of the first-mentioned water-soluble high-molecular additive and containing said additive dissolved in said solution at a concentration of 0.5%~10% (weight/weight basis), while at least a portion of said water-soluble high-molecular additive used here in the washing aqueous solution is allowed during the washing operation to transfer from the washing aqueous solution of the water-soluble high-molecular additive into the surfaces of the particles of said precipitate; and a step of then drying the washed precipitate, to afford the yellow-colored powdery composition consisting essentially of the particles each formed of the homogeneous mixture of the crystallographically stable, amorphous and water-soluble substance of Cefditoren pivoxil with the above-mentioned water-soluble high-molecular additive present in a proportion of 0.5%~5% based on the weight of the Cefditoren pivoxil substance.

In practicing the process of the third aspect of this invention, the acid present in the aqueous solution of the water-soluble high-molecular additive and the acid to be used for the dissolution of the crystalline Cefditoren pivoxil substance may preferably be hydrochloric acid, phosphoric acid, acetic acid or sulfuric acid. Particularly, hydrochloric acid is preferred. The concentration of the acid in said aqueous solution may be within a range of 0.1N~12N, with a range of 0.5N~2.0N being particularly preferred.

The step of dissolving the crystalline Cefditoren pivoxil substance in the acidic aqueous solution containing said water-soluble high-molecular additive and acid may preferably be carried out at a temperature of 10° C. or lower. The dissolution of the crystalline Cefditoren pivoxil substance may preferably be effected with taking a period of time of 10~60 minutes therefor. By adopting these operation conditions, it is necessary to make the Cefditoren pivoxil substance dissolved completely in the aqueous solution of the water-soluble high-molecular additive and the acid.

Next, there is effected the step of neutralizing the resulting aqueous solution of the Cefditoren pivoxil, water-soluble high-molecular additive and acid, with an inorganic base. The aqueous solution of an inorganic base used for this neutralization step may preferably be an aqueous ammonium hydroxide solution, namely aqueous ammonia, or aqueous sodium hydroxide solution, aqueous potassium hydroxide solution, aqueous sodium hydrogen carbonate solution or aqueous potassium hydrogen carbonate solution. Aqueous ammonia is particularly preferred. The concentration of the inorganic base in the aqueous solution of the inorganic base may be in a range of 0.1N~14N, but the base concentration in a range of 0.5N~2.0N is particularly preferred. An aqueous solution of one inorganic base may be used in combination with an aqueous solution of another inorganic base. The addition of the aqueous solution of the inorganic base is preferably carried out slowly, while maintaining the neutralization reaction mixture at a temperature of 0° C.~10° C. The addition may preferably be effected dropwise. The time to be taken for the neutralization reaction may be 5 minutes~24 hours and preferably 5 minutes~10 hours. During the neutralization reaction, it is preferred that the amount of the inorganic base added is so controlled that the resulting reaction mixture shows a pH value of 6.5~7.0 at the completion of the neutralization. With the progress of the neutralization reaction, Cefditoren pivoxil and the water-soluble high-molecular additive are allowed to be co-precipitated simultaneously from the aqueous solution, resulting in the deposition of solid precipitate. This precipitate is composed of a mixture of Cefditoren pivoxil with the water-soluble high-molecular additive.

After the completion of the neutralization reaction, the precipitate is then collected from the resulting neutralization reaction mixture. The collection of the precipitate may be effected by filtration, for example, filtration under a reduced pressure, or by centrifugation, in a conventional manner.

Next, the precipitate so collected is subjected to the step of washing it at a temperature of 10° C. or below with an aqueous solution containing such a water-soluble high-molecular additive which is of the same compound as the high-molecular additive just co-precipitated and thus included in said precipitate and which high-molecular additive is present at a concentration of 0.5%~10% (weight %) in said aqueous solution. By this washing operation, the salts having attached to the precipitate can be removed, and at least a portion of the water-soluble high-molecular additive present in the washing aqueous solution is allowed to transfer into the surface of the precipitate particles from the washing aqueous solution of the water-soluble high-molecular additive during the washing operation. If a plain water were used for the step of washing the precipitate, a portion of the water-soluble high-molecular additive which has been included and contained in the precipitate could be washed away therefrom. In such a possible case, the particles of the powder which could be obtained after a drying of the precipitate so washed with the plain water would be undesirable as the target product wanted, because the content of the water-soluble high-molecular additive in the particles should be unsuitably lower than the desirable one. Such undesirable product is inappropriate in that the Cefditoren pivoxil component contained therein can show some tendency to crystallize out.

The precipitate which has received the washing step as above is then dried in a conventional way. The drying step is preferably carried out at a temperature of 30° C. or lower under a reduced pressure. Thus, as the dried final product, there can be afforded a powdery composition consisting essentially of solid particles which each are formed of a homogeneous mixture of a crystallographically stable, amorphous and water-soluble substance of Cefditoren pivoxil and the water-soluble high-molecular additive as mixed in a proportion of 0.5%~5% (weight %) of said additive, based on the weight of the Cefditoren pivoxil substance.

Preferably, the process of the third aspect of this invention may be effected by such a process comprising a step of dissolving the orthorhombic crystalline substance of Cefditoren pivoxil in an acidic aqueous solution which is containing such a water-soluble high-molecular additive as chosen from hydroxypropylmethyl cellulose, hydroxypropyl cellulose, methyl cellulose and polyvinylpyrrolidone as dissolved at a concentration of 0.05% to 1% (weight/weight basis) and which acidic aqueous solution is containing also hydrochloric acid or phosphoric acid at a concentration of 0.5N~2.0N of the acid, so that the amount of Cefditoren pivoxil dissolved in said acidic aqueous solution is in a range of 10 times to 100 times based on the whole weight of said water-soluble high-molecular additive contained in said acidic aqueous solution, and so that there is prepared an acidic aqueous solution containing Cefditoren pivoxil, the water-soluble high-molecular additive and the acid dissolved therein; a step of subsequently neutralizing the so prepared acidic aqueous solution containing Cefditoren pivoxil, by adding slowly thereto a 1N~2N aqueous sodium hydroxide solution or/and a 1N~2N aqueous sodium hydrogen carbonate solution, or by adding slowly thereto a 1N~2N aqueous ammonium hydroxide solution, with maintaining said acidic aqueous solution at a temperature of 5° C. or below under stirring, until said acidic aqueous solution is neutralized to a pH value of 6.5~7.0; a step of continuing during the neutralization reaction the stirring of the resulting neutralization reaction mixture at a temperature of 5° C. or below, to bring about co-precipitation of Cefditoren pivoxil. and the water-soluble high-molecular additive simultaneously from said aqueous solution; a step of collecting the so deposited precipitate from the resulting neutralization reaction mixture; a step of washing the collected precipitate with an aqueous solution of a water-soluble high-molecular additive made of the substance same as that of the first-mentioned water-soluble high-molecular additive and containing said additive dissolved in said solution at a concentration of 0.5%~10% (weight/weight basis); and a step of then drying the washed precipitate, to afford the yellow-colored powdery composition consisting essentially of the particles each formed of a homogeneous mixture of the amorphous substance of Cefditoren pivoxil with the above-mentioned water-soluble high-molecular additive present in a proportion of 1%~3% based on the weight of the Cefditoren pivoxil substance.

For a process for the preparation of the powdery composition of the second aspect of this invention, there is provided, according to a fourth aspect of this invention, a process for the preparation of a yellow-colored powdery composition consisting essentially of particles which each comprise mixtures of a crystallographically stable, amorphous and water-soluble substance of Cefditoren pivoxil with water-soluble high-molecular additive or additives, and which particles have a uniform, internal texture within each particle, characterized in that the process comprises a step of dissolving an orthorhombic substance of Cefditoren pivoxil in an acidic aqueous solution which is containing a first water-soluble high-molecular additive made of either such a water-solubilized derivative of cellulose as chosen from hydroxy-propylmethyl cellulose, hydroxypropylmethyl cellulose phthalate, hydroxypropyl cellulose, methyl cellulose and a pharmaceutically acceptable alkali metal salt or alkaline earth metal salt of carboxymethyl cellulose, or pluran, carrageenan, polyvinylpyrrolidone or an alginic acid ester of polypropylene glycol as dissolved at a concentration of 0.05%~1% (weight/weight basis) and which acidic aqueous solution is containing also hydrochloric acid, phosphoric acid, sulfuric acid, acetic acid, propionic acid or butyric acid at a concentration of 0.1N~12N of the acid, so that the amount of Cefditoren pivoxil dissolved in said acidic aqueous solution is in a range of 10 times to 130 times based on the whole weight of said first water-soluble high-molecular additive contained in said acidic aqueous solution, and so that there is prepared an acidic aqueous solution containing Cefditoren pivoxil, the first, water-soluble high-molecular additive and the acid dissolved therein; a step of subsequently neutralizing the so prepared acidic aqueous solution, by adding slowly thereto an aqueous solution or solutions of sodium or potassium hydroxide, sodium or potassium hydrogen carbonate, or sodium or potassium carbonate, singly or in combination, or by adding slowly thereto an aqueous solution of ammonium hydroxide, with maintaining said acidic aqueous solution at a temperature of 10° C. or below under stirring, and with the amount of the basic sodium or potassium compound or ammonium hydroxide to be added to said acidic aqueous solution being so adjusted that the reaction solution after the neutralization shows a pH value of 6.5~7.1; a step of continuing during the neutralization reaction the stirring of the aqueous solution containing Cefditoren pivoxil at a temperature of 10° C. or below, to bring about co-precipitation of Cefditoren pivoxil and the first, water-soluble high-molecular additive simultaneously from the aqueous solution; a step of collecting by filtration or centrifugation the so deposited precipitate from the resulting neutralization reaction mixture; a step of washing the collected precipitate with such an aqueous solution which is containing a second, water-soluble high-molecular additive made of a substance different from the above-mentioned first, water-soluble high-molecular additive contained in said acidic aqueous solution containing Cefditoren pivoxil, and which aqueous solution is containing said second high molecular additive dissolved therein at a concentration of 0.5%~10% (weight/weight basis), while at least a portion of said second water-soluble high-molecular additive used here in the washing aqueous solution is allowed during the washing operation to transfer from the washing aqueous solution of the second water-soluble high-molecular additive into the surfaces of the particles of the precipitate; and a step of then drying the washed precipitate, to afford the yellow-colored powdery composition consisting essentially of such particles which each contains Cefditoren pivoxil, and of which the central portion or core portion of each particle is formed only from a homogeneous mixture of the crystallographically stable, amorphous and water-soluble substance of Cefditoren pivoxil with the first water-soluble high-molecular additive present in a proportion of 0.5%~5% based on the weight of said Cefditoren pivoxil substance, and of which the surface layer of each particle is formed from a homogeneous mixture of the crystallographically stable, amorphous and water-soluble substance of Cefditoren pivoxil with said first water-soluble high-molecular additive and also with said second water-soluble high-molecular additive.

The process of the fourth aspect of this invention may be carried out in the same manner as the process of the third aspect of this invention.

The process of the fourth aspect of this invention is preferably effected by such a process comprising a step of dissolving the orthorhombic crystalline substance of Cefditoren pivoxil in an acidic aqueous solution which is containing such a water-soluble high-molecular additive as chosen from hydroxypropylmethyl cellulose, hydroxypropyl cellulose, methyl cellulose and polyvinylpyrrolidone as dissolved at a concentration of 0.05%~1% (weight/weight basis) and which acidic aqueous solution is containing also hydrochloric acid or phosphoric acid at a concentration of 0.5N~2.0N of the acid, so that the amount of Cefditoren pivoxil dissolved in the acidic aqueous solution is in a range of 10 times to 100 times based on the whole weight of said first water-soluble high-molecular additive contained in said acidic aqueous solution, and so that there is prepared an acidic aqueous solution containing Cefditoren pivoxil, the water-soluble high-molecular additive and the acid dissolved therein; a step of subsequently neutralizing the so prepared acidic aqueous solution containing Cefditoren pivoxil, by adding slowly thereto an aqueous 1N~2N sodium hydroxide solution or/and an aqueous 1N~2N sodium hydrogen carbonate solution or by adding slowly thereto an aqueous 1N~2N ammonium hydroxide solution, with maintaining the acidic aqueous solution at a temperature of 5° C. or below under stirring, until the acidic aqueous solution is neutralized to a pH value of 6.5~7.0; a step of continuing the stirring of the neutralization reaction mixture at a temperature of 5° C. or below during the neutralization reaction, to bring about the co-precipitation of Cefditoren pivoxil and said first water-soluble high-molecular additive simultaneously from the aqueous solution; a step of collecting the deposited precipitate from the resulting neutralization reaction mixture; a step of washing the collected precipitate with such an aqueous solution which is containing, as the second water-soluble high-molecular additive made of a substance different from the above-mentioned first water-soluble high-molecular additive, such a water-soluble high-molecular additive as chosen from hydroxypropylmethyl cellulose, hydroxypropyl cellulose, methyl cellulose and polyvinylpyrrolidone, and which aqueous solution is containing said second high-molecular additive dissolved therein at a concentration of 0.5%~10% (weight/weight basis), while at least a portion of the second water-soluble high-molecular additive used here in the washing aqueous solution is allowed during the washing operation to transfer from said aqueous solution of the second water-soluble high-molecular additive into the surfaces of the particles of the precipitate; and a step of then drying the washed precipitate, to afford the yellow-colored powdery composition consisting essentially of such particles of which the central portion or core portion of each particle is formed only from a homogeneous mixture of the amorphous substance of Cefditoren pivoxil with said first water-soluble high-molecular additive, and of which the surface layer of each particle is formed from a homogeneous mixture of the amorphous substance of Cefditoren pivoxil with said first water-soluble high-molecular additive and also with said second water-soluble high-molecular additive.

BEST MODE FOR CARRYING OUT THE INVENTION

Now, this invention is concretely illustrated with reference to typical Examples thereof, but is not limited to these Examples. The crystalline substance of Cefditoren pivoxil used in Example 1~14 given hereinafter is the orthorhombic crystalline substance of Cefditoren pivoxil (mp. 215° C., a purity of about 97% ) obtained in Example 1 of the PCT International Open Laying Publication No. W098/12200.

The following Examples 1~3 illustrate the preparation of the yellow-colored powdery composition according to the first aspect of this invention, and Examples 4~14 illustrate the preparation of the yellow-colored powdery composition according to the second aspect of this invention.

EXAMPLE 1

The crystalline substance (20 g) of 7-[(Z)-2-(2-aminothiazol-4-yl)-2-methoxyiminoacetamido]-3-[(Z)-2-(4-methylthiazol-5-yl)ethenyl]-3-cephem-4-carboxylic acid pivaloyloxymethyl ester, namely Cefditoren pivoxil, was dissolved in an acidic aqueous solution (140 ml) containing hydroxypropyl cellulose (200 mg) as dissolved therein and hydrochloric acid at a concentration of 1N of HCl, with taking a time of 11 minutes for the dissolution of Cefditoren pivoxil therein. During this dissolution operation, the aqueous solution was maintained at a temperature of 5° C. or lower. Thus, there was prepared an acidic aqueous solution (pH 0.6) in which Cefditoren pivoxil had been completely dissolved. This acidic aqueous solution containing Cefditoren pivoxil was then neutralized (to a pH of 7.0) by a dropwise slow addition of a 1N aqueous ammonia (about 138 ml) thereto over a time period of 60 minutes at a temperature of 5° C. or lower. There occurred the deposition of precipitate. The resulting neutralization reaction mixture containing the precipitate as deposited was then stirred overnight at a temperature of 5° C. or lower.

The deposited precipitate was collected by filtration of said reaction mixture, and was then washed well with an aqueous solution of 0.5% (by weight) of hydroxypropyl cellulose (60 ml). The precipitate so washed was dried under a reduced pressure. Thus, there was afforded 19.6 g of a yellow-colored powder (the composition of this invention) consisting essentially of numerous fine particles which each were formed of a homogeneous mixture of the amorphous substance of Cefditoren pivoxil with hydroxypropyl cellulose. When observation was made, under an electron microscope (magnification: x10000), of the surface of the fine particles present in the resulting yellow-colored powder, it was shown that the surface of these fine particles had a simple and uniform phase or texture.

The content of hydroxypropyl cellulose contained in the fine particles present in said resulting yellow-colored powder was calculated, from an analysis by means of a gas chromatography, to be 1% (by weight) on the basis of the Cefditoren pivoxil component. Further, by analyzing said fine particles in the above-mentioned powder X-ray diffraction apparatus, it was found that no peak was appearing in the angle of diffraction in the pattern of the resulting X-ray diffraction chart, and therefore that the Cefditoren pivoxil component present in these fine particles was in the form of the amorphous substance.

EXAMPLE 2

The crystalline substance of Cefditoren pivoxil (5 g) was dissolved in an acidic aqueous solution (35 ml) containing hydroxypropylmethyl cellulose (50 mg) as dissolved therein and 1N HCl, at a temperature of 5° C. or lower and with taking a time of 10 minutes for the dissolution of Cefditoren pivoxil. Thus, there was prepared an acidic aqueous solution (pH 1.32) in which Cefditoren pivoxil had been completely dissolved. The resulting aqueous solution containing Cefditoren pivoxil was then neutralized (up to a pH of 6.9) by a dropwise slow addition of a 1N aqueous ammonia (about 33 ml) thereto over the time period of 30 minutes at a temperature of 5° C. or lower. There occurred the deposition of precipitate. The resulting neutralization reaction mixture was then stirred overnight at a temperature of 5° C. or lower. The deposited precipitate was collected by filtration, and was then washed well with an aqueous solution (15 ml) of 0.5% (by weight) of hydroxy-propylmethyl cellulose. The precipitate so washed was dried under a reduced pressure. Thus, there was afforded 4.9 g of a yellow-colored powder (the composition of this invention) consisting essentially of numerous fine particles which each were formed of a homogeneous mixture of the amorphous substance of Cefditoren pivoxil with hydroxy-propylmethyl cellulose.

The content of hydroxypropylmethyl cellulose contained in the fine particles present in the resulting yellow-colored powder was calculated to be 1% (by weight) on the basis of the Cefditoren pivoxil component. Further, by analyzing said fine particles in the above-mentioned powder X-ray diffraction apparatus, it was found that the Cefditoren pivoxil component present in these fine particles was in the form of the amorphous substance.

EXAMPLE 3

The crystalline substance of Cefditoren pivoxil (5 g) was dissolved in an acidic aqueous solution (35 ml) containing polyvinylpyrrolidone (50 mg) as dissolved therein and HCl at a concentration of 1N, at a temperature of 5° C. or lower and with taking a time of 10 minutes for the dissolution of Cefditoren pivoxil. Thus, there was prepared an acidic aqueous solution (pH 0.4) in which Cefditoren pivoxil was completely dissolved. This aqueous solution was then neutralized by a dropwise slow addition of a 1N aqueous ammonia (about 34 ml) thereto over 30 minutes at a temperature of 5° C. or lower. During the neutralization reaction, precipitate deposited. The resulting neutralization reaction mixture (pH: 6.8) containing the precipitate as formed was stirred at a temperature of 5° C. or lower overnight. The deposited precipitate was collected by filtration, and was then washed well with an aqueous solution (15 ml) of 0.5% (by weight) of polyvinylpyrrolidone. The precipitate so washed was dried under a reduced pressure. Thus, there was obtained 4.9 g of a yellow-colored powder consisting essentially of numerous fine particles which each were formed of a homogeneous mixture of the amorphous substance of Cefditoren pivoxil with polyvinylpyrrolidone.

The content of polyvinylpyrrolidone contained in the fine particles present in the resulting yellow-colored powder was calculated to be 1% (by weight) on the basis of the Cefditoren pivoxil component. By analyzing the said fine particles in the above-mentioned powder X-ray diffraction analyzer, it was found that the Cefditoren pivoxil component existing in these fine particles was in the form of the amorphous substance.

EXAMPLE 4

The crystalline substance of Cefditoren pivoxil (10 g) was dissolved in an acidic aqueous solution (100 ml) containing about 1 g of hydroxypropylmethyl cellulose as dissolved therein (at a concentration of 1%) and HCl at a concentration of 1N, at a temperature of 10° C. or lower. Thus, there was prepared an acidic aqueous solution in which Cefditoren pivoxil was completely dissolved. This acidic aqueous solution obtained was then neutralized by a dropwise slow addition of a iN aqueous sodium hydroxide solution (100 ml) thereto, while the temperature was maintained at 5° C. or lower. During the neutralization reaction, precipitate slowly deposited from the aqueous solution. The resulting neutralization reaction mixture containing the precipitate was stirred overnight at a temperature of 5° C. or lower.

Then, the neutralization reaction mixture was filtered, and the precipitate thus collected was placed in a filtration apparatus which was operated under a reduced pressure. To the filtration apparatus, an aqueous solution of 1% of hydroxypropyl cellulose was added, followed by washing further the precipitate under pushing pressure. The precipitate so washed was dried under a reduced pressure, and there was thus obtained 9.6 g of a yellow-colored powder consisting essentially of numerous fine particles which each were formed from a mixture comprising Cefditoren pivoxil and hydroxypropylmethyl cellulose.

The fine particles present in the resulting yellow-colored powder were examined by a powder X-ray diffraction analyzer (Geigerflex 2027, made by Rigaku Denki K. K. ), to obtain a chart of the powder X-ray diffraction of said fine particles. The result of an analysis of the pattern of the resulting X-ray diffraction chart indicated that no peak was seen in the angle of diffraction in the chart, and that the Cefditoren pivoxil component present in the fine particles was in the form of the amorphous substance.

The total content of hydroxypropylmethyl cellulose plus hydroxypropyl cellulose contained in the fine particles present in the resulting yellow-colored powder was calculated to be 2% (by weight) on the basis of the Cefditoren pivoxil component.

Further, the aqueous solution of hydroxypropyl cellulose which had been used for the washing operation of the precipitate as collected from the neutralization reaction mixture mentioned in the above was then wholly recovered after the washing operation. A measurement was then made of the total residual amount of the hydroxypropyl cellulose remaining in the aqueous solution of hydroxypropyl cellulose which had been used in the washing operation and then recovered as above. The total residual amount so measured of the hydroxypropyl cellulose present in the so recovered aqueous solution after the washing step was observed to be significantly less than the initial, total amount of hydroxylpropyl cellulose which was initially contained in the aqueous solution of hydroxypropyl cellulose as just charged in the washing step. Based on this observed fact, it was deduced that, during the washing operation of the precipitate, an amount of the hydroxypropyl cellulose component present as the solute in the washing aqueous solution had transferred into the precipitate, at least into the surface of the precipitate, from the washing aqueous solution of hydroxypropyl cellulose just employed in said washing step.

Furthermore, when an examination was conducted, under an electron microscope (magnification×10000), in respect of several ones of the fine particles as picked up from the resulting yellow-colored powder as above, it was shown that the surface of these fine particles had a simple and uniform texture or tissue, and further that in the surface of the fine particles, there was substantially not observed any presence of independently separate grains of Cefditoren pivoxil or any presence of independently separate grains of hydroxypropylmethyl cellulose or of hydroxypropyl cellulose.

EXAMPLE 5

The crystalline substance of Cefditoren pivoxil (50 g) was dissolved in an acidic aqueous solution (350 ml) containing hydroxypropylmethyl cellulose (500 mg) as dissolved therein and HCl at a concentration of 1N, at a temperature of 5° C., and with taking the time over a period of 45 minutes for the dissolution of Cefditoren pivoxil. The resulting aqueous solution was filtered through a millipore (1 μm) membrane filter to remove the insoluble solid matters from the solution. Thus, there was prepared an acidic aqueous solution containing Cefditoren pivoxil and hydroxylpropylmethyl cellulose completely dissolved therein, as well as hydrochloric acid.

The resulting acidic aqueous solution here obtained was then neutralized to a pH of 3.3 by a dropwise slow addition of a 1N aqueous sodium hydroxide solution (315 ml), and then to a pH of 7.0 by a slow addition of a 1N aqueous sodium hydrogen carbonate solution (43.5 ml), while the temperature of the resulting reaction solution was maintained at 5° C. or below. The total period of time taken for the dropwise addition of the aqueous solutions of the inorganic bases was 1.5 hours to the completion.

During the neutralization reaction, precipitate slowly deposited. The resulting neutralization reaction solution containing the precipitate as formed was then stirred overnight at a temperature of 5° C. or lower, and then the reaction solution was again adjusted to its pH of 7.0 by a dropwise addition of an aqueous 1N sodium hydrogen carbonate solution.

The neutralization reaction mixture here obtained as above was filtered to recover the precipitate therefrom. The resulting precipitate was washed well with an aqueous solution of 0.5% (by weight) of hydroxypropyl cellulose (150 ml). The precipitate so washed was then dried under a reduced pressure. There was thus obtained 48.5 g of a yellow-colored powder (the composition of this invention) consisting essentially of numerous fine particles which each were substantially formed from a homogeneous mixture comprising the amorphous Cefditoren pivoxil substance and hydroxypropylmethyl cellulose.

The total content of hydroxypropylmethyl cellulose plus hydroxypropyl cellulose contained in the fine particles present in the resulting yellow-colored powder was calculated to be 1.1% (by weight) on the basis of the Cefditoren pivoxil component.

The fine particles present in the resulting yellow-colored powder were placed in a powder X-ray diffraction analyzer for an examination thereof. The result of analysis of the pattern of the X-ray diffraction chart so obtained indicated that no peak was seen in the angle of diffraction in the chart, and therefore that the Cefditoren pivoxil component contained in the fine particles was present in the form of the amorphous substance. Further, when an examination was made under an electron microscope in respect of several ones of the fine particles so obtained, it was shown that the surface of the particles had a simple uniform texture, and that there was substantially not observed the presence of any independently separate grains in the surface of the fine particles.

It is deemed that the fine particles present in the yellow-colored powder as obtained in this Example have such structure that the central portion or core portion of these fine particles is formed of a homogeneous mixture comprising the amorphous substance of Cefditoren pivoxil and hydroxypropylmethyl cellulose, while the surface layer of said fine particles is formed of a homogeneous mixture comprising the amorphous substance of Cefditoren pivoxil, hydroxypropylmethyl cellulose and hydroxypropyl cellulose.

Comparative Example 1

The procedure of Example 5 was repeated in the substantially same manner as in Example 5, except that the use of both the hydroxypropylmethyl cellulose and hydroxypropyl cellulose was completely omitted. In other words, the crystalline substance of Cefditoren pivoxil (5 g) was dissolved in water (50 ml) containing 1N HCl, with taking a period of 23 minutes for the dissolution of Cefditoren pivoxil, while the temperature of the solution was maintained at 5° C. or lower. After the completion of the dissolution of Cefditoren pivoxil in the acidic water, an aqueous 1N sodium hydroxide solution (40 ml) was slowly added dropwise to the resulting acidic aqueous solution of Cefditoren pivoxil to neutralize the latter solution to a pH of 2.1. Then, an aqueous 1N sodium hydrogen carbonate solution (10 ml) was added dropwise to the aqueous solution of Cefditoren pivoxil to neutralize the solution further. During the neutralization step, the reaction solution was maintained at a temperature of 5° C. or lower. Total time taken for the completion of the addition of these aqueous solutions of the inorganic bases was 27 minutes.

The resulting neutralization reaction mixture containing the precipitate as formed (pH 6.2) was stirred for 1.5 hours at a temperature of 5° C. or lower, and then was neutralized further to a pH of 7.0 by a dropwise addition of an aqueous 1N sodium hydrogen carbonate solution.

During the latter neutralization reaction step, precipitate of Cefditoren pivoxil deposited from the aqueous solution. The neutralization reaction mixture obtained here was stirred at a temperature of 5° C. or lower overnight.

The here obtained neutralization reaction mixture containing the precipitate was filtered to recover the deposited precipitate. The precipitate so collected was washed well with water (25 ml) as cooled to 5° C. The precipitate so washed was dried to afford a fine powder (4.4 g) which was formed of a crystalline substance of Cefditoren pivoxil. The fine particles present in said fine powder was examined by the powder X-ray diffraction analyzer, to indicate that a peak was appearing in the angle of diffraction in the pattern of the resulting X-ray diffraction chart. It was thus deduced that the Cefditoren pivoxil component contained in the fine powder obtained here was present in the form of a crystalline substance.

EXAMPLE 6

The crystalline substance of Cefditoren pivoxil (50 g) was dissolved over 45 minutes in an acidic aqueous solution (350 ml) containing hydroxypropylmethyl cellulose (500 mg) as dissolved therein and HCl at a concentration of 1N at a temperature of 5° C. or lower. The resulting aqueous solution containing Cefditoren pivoxil was filtered through a millipore (1 μm) membrane filter to remove the insoluble solid matters therefrom. Thus, there was prepared an acidic aqueous solution in which Cefditoren pivoxil, hydroxypropylmethyl cellulose and hydrochloric acid were completely dissolved.

The acidic aqueous solution obtained here was neutralized to a pH of 7.0 by a dropwise slow addition of a 1N aqueous ammonia, namely an aqueous solution of 1N ammonium hydroxide (331 ml), while the acidic aqueous solution was maintained at a temperature of 5° C. or lower. The total time taken for the completion of the dropwise addition of the aqueous ammonia was 1.5 hours. During this neutralization reaction, precipitate slowly deposited. The resulting neutralization reaction mixture containing the precipitate as formed was then stirred overnight at a temperature of 5° C. or lower. Then, the pH of the reaction mixture was again adjusted to a pH of 7.0 by a dropwise addition of a 1N aqueous ammonia.

The neutralization reaction mixture here obtained as above was filtered to recover the precipitate therefrom. The resulting precipitate was washed well with an aqueous solution of 0.5% (by weight) of hydroxypropyl cellulose (150 ml). The precipitate so washed was then dried under a reduced pressure. There was thus obtained 48.8 g of a yellow-colored powder (the composition of this invention) consisting essentially of numerous fine particles which each were formed substantially from a homogeneous mixture comprising the amorphous substance of Cefditoren pivoxil and hydroxypropylmethyl cellulose.

The fine particles present in the resulting yellow-colored powder was analyzed by a high performance liquid chromatography, to detect that the fine particles had a content of 96% (by weight) of the Cefditoren pivoxil component based on the weight of the fine particles. Further, the total content of hydroxypropylmethyl cellulose plus hydroxypropyl cellulose contained in the fine particles was calculated to be 1.3% (by weight) based on the weight of the Cefditoren pivoxil component.

The fine particles present in the resulting yellow-colored powder were placed in and examined by the powder X-ray diffraction analyzer (Geigerflex 2027, made by Rigaku Denki K. K.), to give a chart of the powder X-ray diffraction of said fine particles. The result of analysis of the pattern of the X-ray diffraction chart revealed that no peak was seen in the angle of diffraction in the chart, and therefore that the Cefditoren pivoxil component contained in the fine particles was present in the form of the amorphous substance. Further, the examination was made under an electron microscope in respect of several ones of the fine particles, it was shown that the surface of the fine particles had a simple and uniform texture and further that any independently separate grains are substantially absent in the surface of the fine particles.

It is deemed that the fine particles present in the yellow-colored powder as obtained in this Example have such structure that the central portion or core portion of these fine particles is formed of a homogeneous mixture comprising the amorphous substance of Cefditoren pivoxil and hydroxypropylmethyl cellulose, while the surface layer of the fine particles is formed of a homogeneous mixture comprising the amorphous substance of Cefditoren pivoxil and hydroxypropylmethyl cellulose and hydroxypropyl cellulose.

Figure 1:
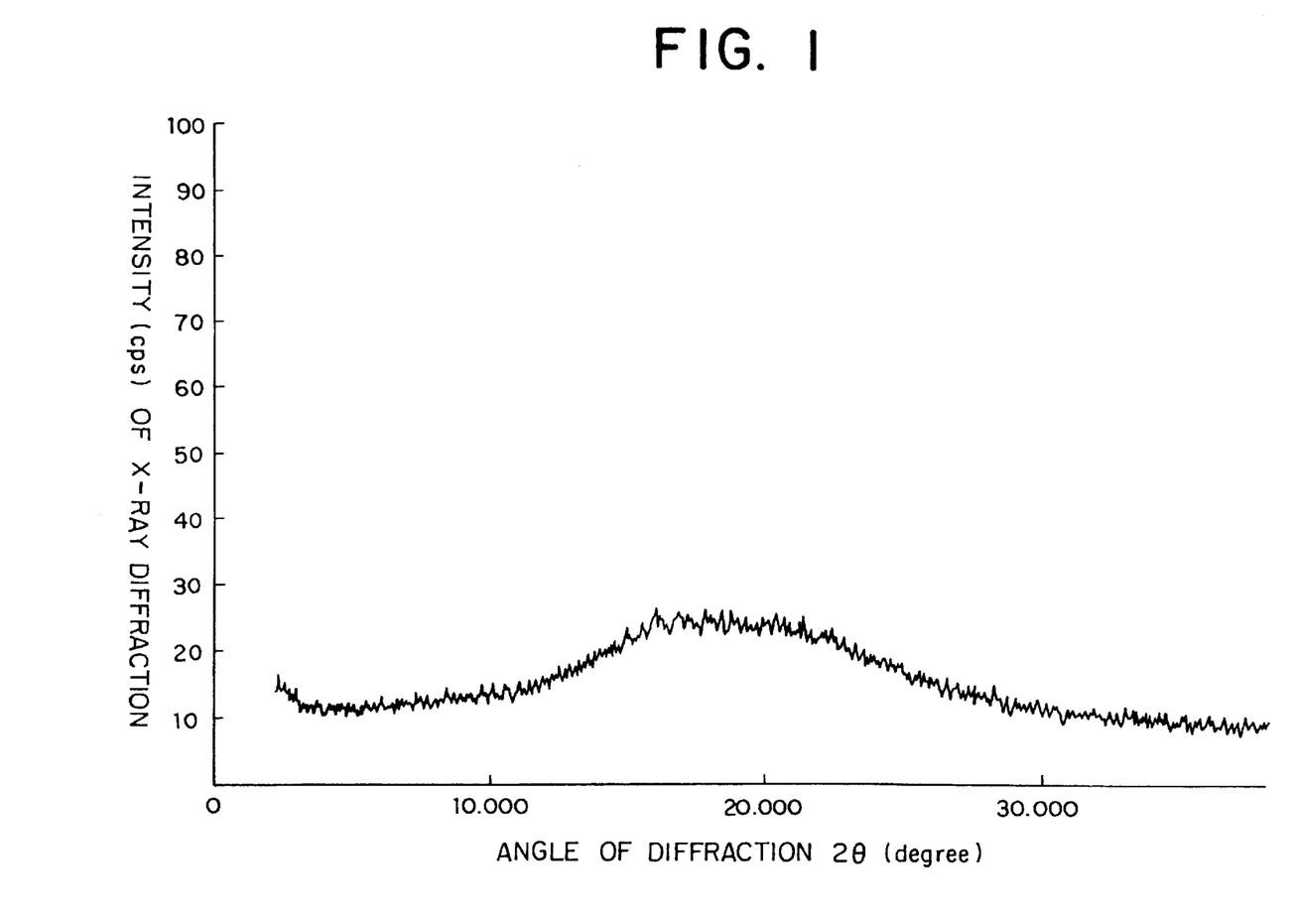
FIG. 1 shows a pattern of a powder X-ray diffraction chart obtained by measuring in a powder X-ray diffractometer the powdery composition which consists essentially of particles as formed from a homogeneous mixture of the amorphous substance of Cefditoren pivoxil with hydroxypropylmethyl cellulose, and which was produced in Example 6 of this invention given hereinafter.

A diffraction chart of the powder X-ray diffraction which was given by measuring the fine particles of the yellow-colored powder as produced in this Example in the powder X-ray diffraction analyzer (Geigerflex 2027, made by Rigaku Denki K. K.), is shown in FIG. 1 of the attached drawings.

Figure 2A:
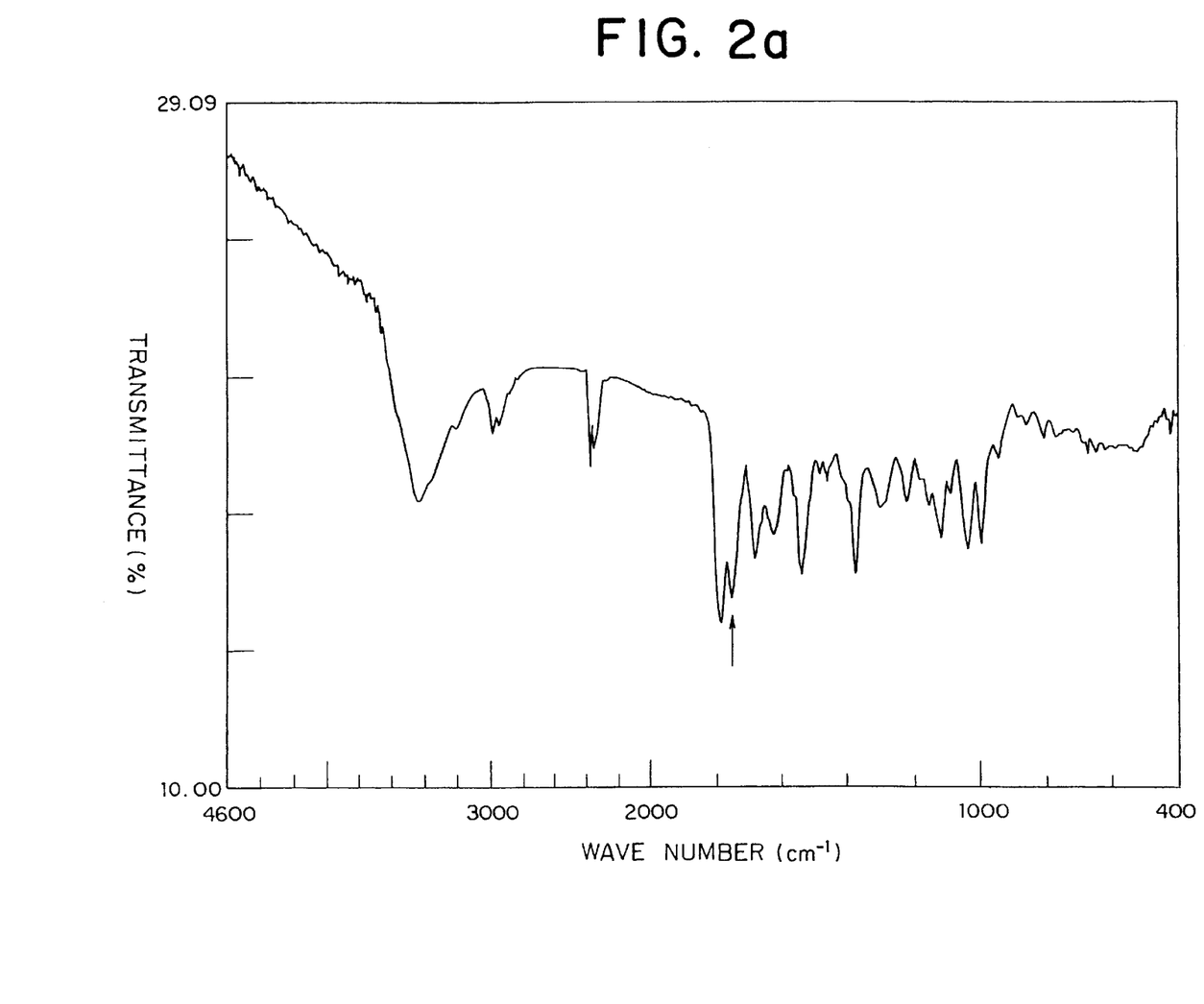
FIG. 2a shows an infrared absorption spectrum (as measured by the pelleted KBr method) of the Cefditoren pivoxil component contained in the particles which are essentially formed from the homogeneous mixture of the amorphous substance of Cefditoren pivoxil with hydroxypropylmethyl cellulose, and which were produced in Example 6 of this invention given hereinafter.

An infrared absorption spectrum (measured by the pelleted KBr method) of the amorphous substance of Cefditoren pivoxil present in the fine particles just mentioned above was also measured by placing said fine particles in an infrared spectrometer.

Figure 2B:
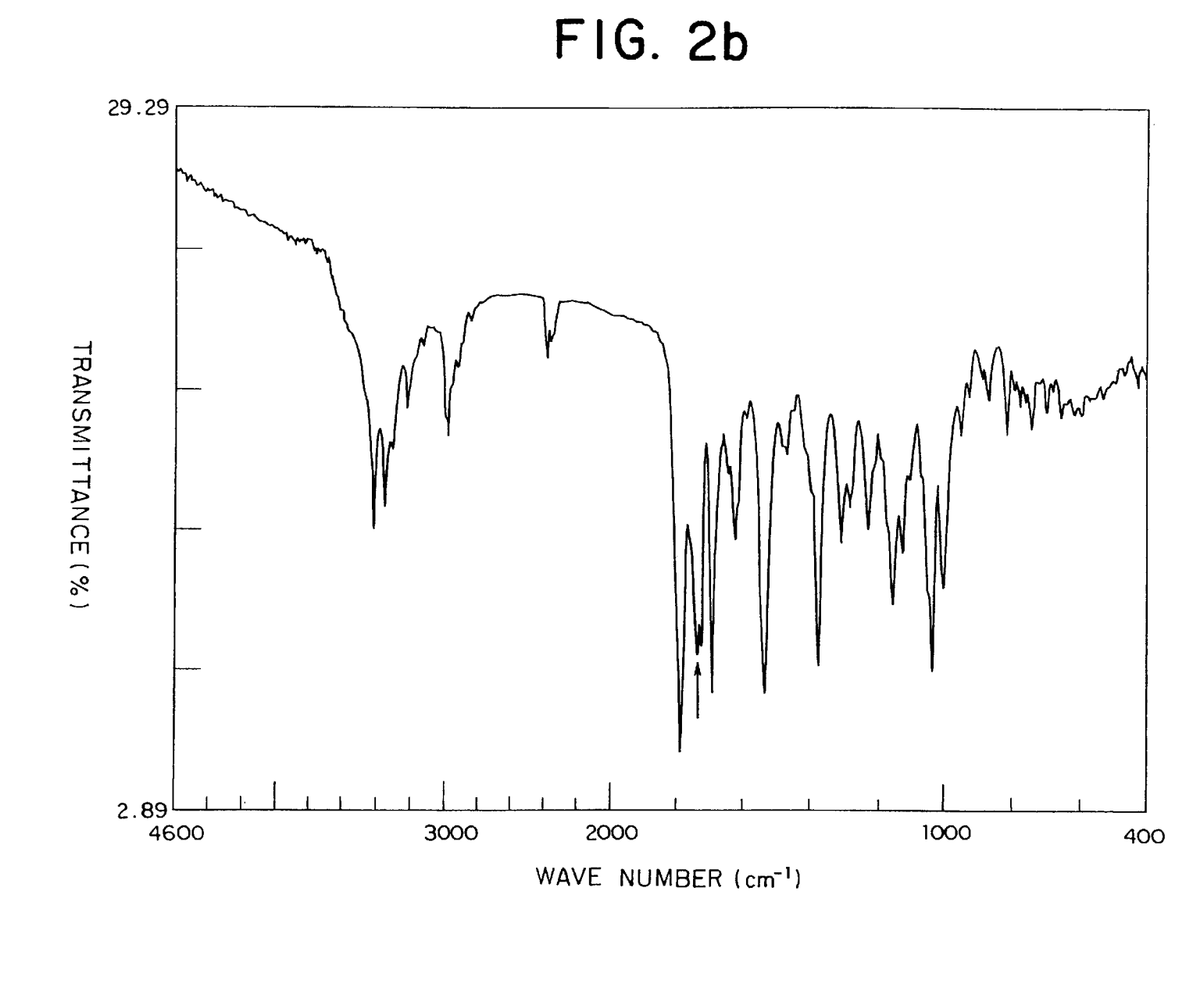
FIG. 2b shows an infrared absorption spectrum (as measured by the pelleted KBr method) of the crystalline substance of Cefditoren pivoxil (which is the orthorhombic crystalline substance as obtained in Example 1 of the PCT International Open-Laying Publication No. W098/12200). The arrows given in these charts of the infrared absorption spectra indicate the absorption peaks at the wave number of 1750 $cm^{-1}$.

The chart of the infrared absorption spectrum thus obtained is shown in FIG. 2a of the attached drawings. An infrared absorption spectrum was similarly measured for the crystalline substance of Cefditoren pivoxil used in this Example as the starting material, and the measured chart thereof is also shown in FIG. 2b of the attached drawings.

Comparative Example 2

The procedure of Example 6 was repeated insubstantially the same manner as in Example 6, except that the use of both of hydroxypropylmethyl cellulose and hydroxypropyl cellulose was omitted.

Namely, Cefditoren pivoxil in the form of a crystalline substance(20 g) was dissolved over 3 hours in a volume of water (190 ml) containing HCl at a concentration of 1N, at a temperature of 5° C. or lower. After the completion of the dissolution of Cefditoren pivoxil in the acidified water, the resulting aqueous solution was filtered through a millipore (1.0 μm) membrane filter. The resulting acidic aqueous solution containing Cefditoren pivoxil was then neutralized to a pH of 6.03 by a dropwise slow addition of a 1N aqueous ammonia (192 ml), while the acidic solution was maintained at a temperature of 5° C. or lower. The resulting neutralization reaction mixture containing the precipitate as formed (pH 6.03) was stirred overnight at a temperature of 5° C. or lower, and then 1N aqueous ammonia was again added dropwise to adjust the pH of the reaction mixture to pH 5.8. During this step of the neutralization reaction, precipitate of Cefditoren pivoxil deposited from the aqueous solution. The neutralization reaction mixture obtained here was stirred at a temperature of 5° C. or lower overnight.

The resultant neutralization reaction mixture containing the precipitate was filtered to recover the deposited precipitate. The collected precipitate was washed well with cold water at 5° C. (60 ml). The precipitate so washed was dried to afford a fine powder (19.4 g) which was formed of a crystalline substance of Cefditoren pivoxil. The resulting fine powder obtained here was examined by the powder X-ray diffraction analyzer, to indicate that a peak was appearing in the angle of diffraction in the pattern of the X-ray diffraction chart so obtained. It is thus confirmed that the Cefditoren pivoxil component contained in the resulting fine particles was present in the crystalline substance form.

EXAMPLE 7

The crystalline substance of Cefditoren pivoxil (5 g) was dissolved over 16 minutes in an acidic aqueous solution (35 ml) containing hydroxypropylmethyl cellulose (50 mg) as dissolved therein and HCl at a concentration of 1N, at a temperature of 5° C. or lower. Thus, there was prepared an acidic aqueous solution (pH 0.8) in which Cefditoren pivoxil, hydroxypropylmethyl cellulose and hydrochloric acid were completely dissolved.

The resulting acidic aqueous solution was neutralized to a pH of 6.7 by a dropwise slow addition of a 1N aqueous ammonia (about 34 ml), while the acidic aqueous solution was maintained at a temperature of 5° C. or lower. The time taken for the completion of the dropwise addition of the aqueous ammonia was 33 minutes. During the neutralization reaction, precipitate slowly deposited. The resulting neutralization reaction mixture containing the precipitate as formed was stirred overnight at a temperature of 5° C. or lower.

The neutralization reaction mixture obtained here was filtered to collect the precipitate. The resulting precipitate was washed well with an aqueous solution of a 0.5% (by weight) of hydroxypropyl cellulose (75 ml). The precipitate so washed was then dried under a reduced pressure. There was thus obtained 4.8 g of a yellow-colored powder (the composition of this invention) consisting essentially of numerous fine particles which each were formed substantially from a homogeneous mixture comprising the amorphous substance of Cefditoren pivoxil and hydroxypropylmethyl cellulose.

The total content of hydroxypropylmethyl cellulose and hydroxypropyl cellulose contained in the fine particles present in the resulting yellow-colored powder was calculated to be 1.1% (by weight) based on the weight of the Cefditoren pivoxil component.

The fine particles obtained here were placed in and examined by the powder X-ray diffraction analyzer. The result of analysis of the pattern of the resulting X-ray diffraction chart indicated that no peak was seen in the angle of diffraction, and therefore that the Cefditoren pivoxil component contained in the fine particles was present in the form of the amorphous substance. Further, an examination was made under an electron microscope in respect of several ones of the fine particles to show that the surface of the fine particles had a simple and uniform phase or texture.

It is deemed that the fine particles present in the yellow-colored powder as obtained in this Example have such structure that the central portion or core portion of these fine particles is formed of a homogeneous mixture comprising the amorphous substance of Cefditoren pivoxil and hydroxypropylmethyl cellulose, while the surface layer of the fine particles is formed of a homogeneous mixture comprising the amorphous substance of Cefditoren pivoxil, hydroxypropylmethyl cellulose and hydroxypropyl cellulose.

EXAMPLE 8

The crystalline substance of Cefditoren pivoxil (5 g) was dissolved over 10 minutes in an acidic aqueous solution (35 ml) containing hydroxypropylmethyl cellulose (100 mg) as dissolved therein and HCl at a concentration of 1N, at a temperature of 5° C. or lower. Thus, there was prepared an acidic aqueous solution (pH 0.7) in which Cefditoren pivoxil, hydroxypropylmethyl cellulose and hydrochloric acid were completely dissolved.

The acidic aqueous solution obtained here was neutralized to a pH of 7.0 by a dropwise slow addition of a 1N aqueous ammonia (about 34 ml), while the acidic aqueous solution being maintained at a temperature of 5° C. or lower. The time taken for the completion of the dropwise addition of the aqueous ammonia was 30 minutes. During the neutralization reaction, precipitate slowly deposited. The so obtained neutralization reaction solution containing the precipitate was stirred at a temperature of 5° C. or lower overnight.

The neutralization reaction mixture obtained as above was filtered to collect the precipitate. The resulting precipitate was washed well with an aqueous solution of 0.5% (by weight) of hydroxypropyl cellulose (15 ml). The precipitate so washed was then dried under a reduced pressure. There was thus obtained 5 g of a yellow-colored powder (the composition of this invention) consisting essentially of numerous fine particles which each were formed substantially from a homogeneous mixture comprising the amorphous substance of Cefditoren pivoxil and hydroxypropylmethyl cellulose.

The total content of hydroxypropylmethyl cellulose plus hydroxypropyl cellulose contained in the fine particles present in the resulting yellow-colored powder was calculated to be 2.0% (by weight) based on the weight of the Cefditoren pivoxil component.

The fine particles obtained were placed in and examined by the powder X-ray diffraction analyzer. The result of analysis of the pattern of the resulting X-ray diffraction chart indicated that no peak was appearing in the angle of diffraction, and therefore that the Cefditoren pivoxil component contained in the fine particles was present in the form of the amorphous substance.

It is deemed that the fine particles present in the yellow-colored powder as obtained in this Example have such structure that the central portion or core portion of these fine particles is formed of a homogeneous mixture comprising the amorphous substance of Cefditoren pivoxil and hydroxypropylmethyl cellulose, but the surface layer of the fine particles is formed of a homogeneous mixture comprising the amorphous substance of Cefditoren pivoxil, hydroxypropylmethyl cellulose and hydroxypropyl cellulose.

EXAMPLE 9

The crystalline substance of Cefditoren pivoxil (5 g) was dissolved over 10 minutes in an acidic aqueous solution (35 ml) containing hydroxypropylmethyl cellulose (40 mg) as dissolved therein and HCl at a concentration of 1N at a temperature of 5° C. or lower. Thus, there was prepared an acidic aqueous solution (pH 0.4) in which Cefditoren pivoxil, hydroxypropylmethyl cellulose and hydrochloric acid were completely dissolved.

The resulting acidic aqueous solution obtained here was neutralized to a pH of 6.9 by a dropwise slow addition of a 1N aqueous ammonia (about 34 ml), while the acidic aqueous solution being maintained at a temperature of 5° C. or lower. The time taken for the completion of the dropwise addition of the aqueous ammonia was 30 minutes. During the neutralization reaction, precipitate slowly deposited. The resulting neutralization reaction solution containing the precipitate as formed was stirred overnight at a temperature of 5° C. or lower.

The neutralization reaction mixture obtained as above was then filtered to collect the precipitate. The resulting precipitate was washed well with an aqueous solution of 0.5% (by weight) of hydroxypropyl cellulose (15 ml). The precipitate so washed was then dried under a reduced pressure. There was thus obtained 5 g of a yellow-colored powder (the composition of this invention) consisting essentially of numerous fine particles which each were formed substantially from a homogeneous mixture comprising the amorphous substance of Cefditoren pivoxil and hydroxypropylmethyl cellulose.

The total content of hydroxypropylmethyl cellulose and hydroxypropyl cellulose contained in the fine particles present in the resulting yellow-colored powder was calculated to be 1.1% (by weight) based on the weight of the Cefditoren pivoxil component.

The fine particles thus obtained were placed in and examined by the powder X-ray diffraction analyzer. The result of analysis of the pattern of the resulting X-ray diffraction chart indicated that no peak was appearing in the angle of diffraction, and therefore that the Cefditoren pivoxil component contained in the fine particles was present in the form of the amorphous substance.

It is deemed that the fine particles present in the yellow-colored powder as obtained in this Example have such structure that the central portion or core portion of these fine particles is formed of a homogeneous mixture comprising the amorphous substance of Cefditoren pivoxil and hydroxypropylmethyl cellulose, but the surface layer of the fine particles is formed of a homogeneous mixture comprising the amorphous substance of Cefditoren pivoxil, hydroxypropylmethyl cellulose and hydroxypropyl cellulose.

EXAMPLE 10

The crystalline substance of Cefditoren pivoxil (5 g) was dissolved over 10 minutes in an acidic aqueous solution (35 ml) containing hydroxypropyl cellulose (50 mg) as dissolved therein and HCl at a concentration of 1N at a temperature of 5° C. or lower. Thus, there was prepared an acidic aqueous solution (pH 0.7) in which Cefditoren pivoxil, hydroxypropyl cellulose and hydrochloric acid were completely dissolved.

The resulting acidic aqueous solution obtained here was neutralized to a pH of 6.7 by a dropwise slow addition of a 1N aqueous ammonia (about 34 ml), while the acidic aqueous solution being maintained at a temperature of 5° C. or lower. The time taken for the completion of the dropwise addition of the aqueous ammonia was 36 minutes. During the neutralization reaction, precipitate slowly deposited. The resulting neutralization reaction solution containing the precipitate as formed was stirred overnight at a temperature of 5° C. or lower.

The neutralization reaction mixture obtained as above was filtered to collect the precipitate. The resulting precipitate was washed well with an aqueous solution of 0.5% (by weight) of hydroxypropylmethyl cellulose (15 ml). The precipitate so washed was then dried under a reduced pressure. There was thus obtained 5 g of a yellow-colored powder (the composition of this invention) consisting essentially of numerous fine particles which each were formed substantially from a homogeneous mixture comprising the amorphous substance of Cefditoren pivoxil and hydroxypropyl cellulose.

The total content of hydroxypropyl cellulose and hydroxypropylmethyl cellulose contained in the fine particles present in the resulting yellow-colored powder was calculated to be 1% (by weight) based on the weight of the Cefditoren pivoxil component.

The fine particles thus obtained were placed in and examined by the powder x-ray diffraction analyzer. The result of analysis of the pattern of the resulting x-ray diffraction chart indicated that no peak was appearing in the angle of diffraction in said chart, and therefore that the Cefditoren pivoxil component contained in the fine particles was present in the form of the amorphous substance.

It is deemed that the fine particles present in the yellow-colored powder as obtained in this Example have such structure that the central portion or core portion of these fine particles is formed of a homogeneous mixture comprising the amorphous substance of Cefditoren pivoxil and hydroxypropyl cellulose, but the surface layer of the fine particles is formed of a homogeneous mixture comprising the amorphous substance of Cefditoren pivoxil, hydroxypropyl cellulose and hydroxypropylmethyl cellulose.

EXAMPLE 11

The crystalline substance of Cefditoren pivoxil (5 g) was dissolved over 10 minutes in an acidic aqueous solution (35 ml) containing hydroxypropyl cellulose (50 mg) as dissolved therein and HCl at a concentration of 1N at a temperature of 5° C. or lower. Thus, there was prepared an acidic aqueous solution (pH 0.3) in which Cefditoren pivoxil, hydroxypropyl cellulose and hydrochloric acid were completely dissolved.

The resulting acidic aqueous solution obtained here was neutralized to a pH of 6.9 by a dropwise slow addition of a 1N aqueous ammonia (about 34.5 ml), while the acidic aqueous solution being maintained at a temperature of 5° C. or lower. The time taken for the completion of the dropwise addition of the aqueous ammonia was 43 minutes. During the neutralization reaction, precipitate slowly deposited. The resulting neutralization reaction solution containing the precipitate as formed was stirred at a temperature of 5° C. or lower overnight.

The neutralization reaction mixture obtained as above was filtered to collect the precipitate. The resulting precipitate was washed well with an aqueous solution of 0.5% (by weight) of methyl cellulose (15 ml). The precipitate so washed was then dried under a reduced pressure. There was thus obtained 4.9 g of a yellow-colored powder (the composition of this invention) consisting essentially of numerous fine particles which each were formed substantially from a homogeneous mixture comprising the amorphous substance of Cefditoren pivoxil and hydroxypropyl cellulose.

The total content of hydroxypropyl cellulose and methyl cellulose contained in the fine particles present in the resulting yellow-colored powder was calculated to be 1% (by weight) based on the weight of the Cefditoren pivoxil component.

The fine particles thus obtained were placed in and examined by the powder X-ray diffraction analyzer. The result of analysis of the pattern of the resulting X-ray diffraction chart indicated that no peak was appearing in the angle of diffraction in said chart, and therefore that the Cefditoren pivoxil component contained in the fine particles was present in the form of the amorphous substance.

It is deemed that the fine particles contained in the yellow-colored powder as obtained in this Example have such structure that the central portion or core portion of these fine particles is formed of a homogeneous mixture comprising the amorphous substance of Cefditoren pivoxil and hydroxypropyl cellulose, but the surface layer of the fine particles is formed of a homogeneous mixture comprising the amorphous substance of Cefditoren pivoxil, hydroxypropyl cellulose and methyl cellulose.

EXAMPLE 12

The crystalline substance (5 g) was dissolved over 10 minutes in an acidic aqueous solution (35 ml) containing hydroxypropylmethyl cellulose (50 mg) as dissolved therein and 1N—HCl at a temperature of 5° C. or lower. Thus, there was prepared an acidic aqueous solution (pH 1.1) in which Cefditoren pivoxil, hydroxypropylmethyl cellulose and hydrochloric acid were completely dissolved.

The resulting acidic aqueous solution obtained here was neutralized to a pH of 7.0 by a dropwise slow addition of a 1N aqueous ammonia (about 34 ml) , while the acidic aqueous solution being maintained at a temperature of 5° C. or lower. The time taken for the completion of the dropwise addition of the aqueous ammonia was 50 minutes. During the neutralization reaction, precipitate slowly deposited. The resulting neutralization reaction solution containing the precipitate as formed was stirred at a temperature of 5° C. or lower overnight.

The neutralization reaction mixture here obtained as above was filtered to collect the precipitate. The resulting precipitate was washed well with an aqueous solution of 0.5% (by weight) of hydroxypropyl cellulose (15 ml). The precipitate so washed was then dried under a reduced pressure. There was thus obtained 4.9 g of a yellow-colored powder (the composition of this invention) consisting essentially of numerous fine particles which each were formed substantially from a homogeneous mixture comprising the amorphous substance of Cefditoren pivoxil and hydroxypropylmethyl cellulose.

The total content of hydroxypropylmethyl cellulose and hydroxypropyl cellulose contained in the fine particles present in the resulting yellow-colored powder was calculated to be 1.1% (by weight) based on the weight of the Cefditoren pivoxil component.

The fine particles thus obtained were placed in and examined by the powder X-ray diffraction analyzer. The result of analysis of the pattern of the resulting X-ray diffraction chart indicated that no peak was appearing in the angle of diffraction in the chart, and therefore that the Cefditoren pivoxil component contained in the fine particles was present in the form of the amorphous substance.

It is deemed that the fine particles contained in the yellow-colored powder as obtained in this Example have such structure that the central portion or core portion of these fine particles is formed of a homogeneous mixture comprising the amorphous substance of Cefditoren pivoxil and hydroxypropylmethyl cellulose, but the surface layer of the fine particles is formed of a homogeneous mixture comprising the amorphous substance of Cefditoren pivoxil, hydroxypropylmethyl cellulose and hydroxypropyl cellulose.

EXAMPLE 13

The crystalline substance of Cefditoren pivoxil (5 g) was dissolved over 16 minutes in an acidic aqueous solution (35 ml) containing methyl cellulose (50 mg) as dissolved therein and HCl at a concentration of 1N, at a temperature of 5° C. or lower. Thus, there were prepared an acidic aqueous solution (pH 0.4) in which Cefditoren pivoxil, methyl cellulose and hydrochloric acid were completely dissolved.

The resulting acidic aqueous solution obtained here was neutralized to a pH of 6.7 by a dropwise slow addition of a 1N aqueous ammonia (about 34 ml), while the acidic aqueous solution being maintained at a temperature of 5° C. or lower. The time taken for the completion of the dropwise addition of the aqueous ammonia was 40 minutes. During the neutralization reaction, precipitate slowly deposited. The resulting neutralization reaction solution containing the precipitate as formed was stirred at a temperature of 5° C. or lower overnight.

The neutralization reaction mixture here obtained as above was filtered to collect the precipitate. The resulting precipitate was washed well with an aqueous solution of 0.5% (by weight) of hydroxypropyl cellulose (15 ml). The precipitate so washed was then dried under a reduced pressure. There was thus obtained 4.9 g of a yellow-colored powder (the composition of this invention) consisting essentially of numerous fine particles which each were formed substantially from a homogeneous mixture comprising the amorphous substance of Cefditoren pivoxil and methyl cellulose.

The total content of methyl cellulose and hydroxypropyl cellulose contained in the fine particles present in the resulting yellow-colored powder was calculated to be 2% (by weight) based on the weight of the Cefditoren pivoxil component.

The fine particles thus obtained were placed in and examined by the powder X-ray diffraction analyzer. The result of analysis of the pattern of the resulting X-ray diffraction chart indicated that no peak was appearing in the angle of diffraction in the chart, and therefore that the Cefditoren pivoxil component contained in the fine particles was present in the form of the amorphous substance.

It is deemed that the fine particles present in the yellow-colored powder as obtained in this Example have such structure that the central portion or core portion of these fine particles is formed of a homogeneous mixture comprising the amorphous substance of Cefditoren pivoxil and methyl cellulose, but the surface layer of the fine particles is formed of a homogeneous mixture comprising the amorphous substance of Cefditoren pivoxil, methyl cellulose and hydroxypropyl cellulose.

EXAMPLE 14

The crystalline substance of Cefditoren pivoxil (5 g) as dissolved over 10 minutes in an acidic aqueous solution (35 ml) containing methyl cellulose (50 mg) as dissolved therein and HCl at a concentration of 1N at a temperature of 5° C. or lower. Thus, there was prepared an acidic aqueous solution (pH 0.3) in which Cefditoren pivoxil, methyl cellulose and hydrochloric acid were completely dissolved.

The resulting acidic aqueous solution obtained here was then neutralized to a pH of 6.7 by a dropwise slow addition of a 1N aqueous ammonia (about 34.5 ml), while the acidic aqueous solution being maintained at a temperature of 5° C. or lower. The time taken for the completion of the dropwise addition of the aqueous ammonia was 23 minutes. During the neutralization reaction, precipitate slowly deposited. The resulting neutralization reaction solution containing the precipitate as produced was stirred at a temperature of 5° C. or lower overnight.

The neutralization reaction mixture obtained as above was filtered to collect the precipitate. The resulting precipitate was washed well with an aqueous solution of 0.5% (by weight) of hydroxypropylmethyl cellulose (15 ml). The precipitate so washed was then dried under a reduced pressure. There was thus obtained 4.9 g of a yellow-colored powder (the composition of this invention) consisting essentially of numerous fine particles which each were formed substantially from a homogeneous mixture comprising the amorphous substance of Cefditoren pivoxil and methyl cellulose.

The total content of methyl cellulose and hydroxyropylmethyl cellulose contained in the fine particles present in the resulting yellow-colored powder was calculated to be 1.1% (by weight) based on the weight of the Cefditoren pivoxil component.

The fine particles thus obtained were placed in and examined by the powder X-ray diffraction analyzer. The result of analysis of the pattern of the resulting X-ray diffraction chart indicated that no peak was appearing in the angle of diffraction in the chart, and therefore that the Cefditoren pivoxil component contained in the fine particles was present in the form of the amorphous substance.

It is deemed that the fine particles contained in the yellow-colored powder as obtained in this Example have such structure that the central portion or core portion of these fine particles is formed of a homogeneous mixture comprising the amorphous substance of Cefditoren pivoxil and methyl cellulose, but the surface layer of the fine particles is formed of a homogeneous mixture comprising the amorphous substance of Cefditoren pivoxil, methyl cellulose and hydroxypropylmethyl cellulose.

Test Example 1

There was taken as a sample one gram of the yellow-colored powder (the composition of this invention), which was obtained in Example 6 above, and which consisted essentially of the particles as formed substantially from a homogeneous mixture comprising the amorphous substance of Cefditoren pivoxil and hydroxypropylmethyl cellulose, and in which the surface layer of said particles contained additionally hydroxypropyl cellulose. The sample so taken was placed in 250 ml of an acidic water (pH 1.2) containing about 1N HCl at 37° C. and stirred at 37° C. for 2 hours. The resulting aqueous solution was passed through a millipore (1 μm) membrane filter to remove the insoluble solid therefrom. The transparent aqueous solution here obtained, which contained Cefditoren pivoxil and the water-soluble cellulose derivatives above-mentioned as dissolved therein, was then measured in respect of the concentration of the Cefditoren pivoxil. By this measuring test, the amorphous substance of Cefditoren pivoxil contained in said yellow-colored powder was found to have a solubility of at least 4 mg/ml in said acidic water at 37° C.

On the other hand, a test similar to that given in the above was carried out to measure the solubility of the crystalline substance of Cefditoren pivoxil (the orthorhomic crystalline substance of Cefditoren pivoxil as obtained in Example 1 of the PCT application International Open-Laying Publication No. W098/12200), which was used as the starting material. This crystalline substance of Cefditoren pivoxil was found to have a solubility of only about 0.4 mg/ml in the above-mentioned acidic water at 37° C.

Test Example 2

Five grams of the yellow-colored powdery composition as obtained in the above Example 6 were placed in a sealed container and then stored therein at 40° C. under an atmosphere of dry air for 4 months. After the storage, the yellow-colored powdery composition was taken out from the container, and measured for its X-ray diffraction in the powder X-ray diffraction analyzer same as that used in Example 6. An analysis of the pattern of the resulting X-ray diffraction chart indicated that no peak was appearing in the angle of diffraction in the chart. It was thus found that the Cefditoren pivoxil contained in the fine particles present in the above-mentioned yellow-colored powder, even after its storage at 40° C. for 4 months, could remain in the form of the amorphous substance and therefore has a crystallographical stability.

Industrial Applicability

The yellow-colored powdery composition consisting essentially of the particles as formed from a homogeneous mixture of the amorphous substance of Cefditoren pivoxil with a water-soluble high-molecular additive, for example, a water-solubilized cellulose derivative is now provided according to this invention, and said composition is orally administrable and is useful as such an orally administrable antibacterial agent which has a broad antibacterial spectrum. The Cefditoren pivoxil component contained in this composition has a high solubility in an HCl-acidified water having a pH value of about 1.2 and hence the composition of this invention can exhibit a high therapeutic efficacy when administered orally.

We claim:

1. An orally administrable, yellow-colored powdery composition consisting essentially of solid particles which each are formed of a homogeneous mixture of a crystallographically stable, amorphous and water-soluble substance of Cefditoren pivoxil with a water-soluble high-molecular additive, and which particles have a uniform, internal texture within each particle, characterized in that said yellow-colored powdery composition consists essentially of the solid particles each formed of the homogeneous mixture of (i) the crystallographically stable, amorphous and water-soluble substance of Cefditoren pivoxil, namely 7-[(Z)-2-(2-aminothiazol-4-yl)-2-methoxyiminoacetamido]-3-[(Z)-2-(4-methylthiazol-5-yl)ethenyl]-3-cephem-4-carboxylic acid pivaloyloxymethyl ester, with (ii) the water-soluble high-molecular additive which is either such a pharmaceutically acceptable, water-solubilized derivative of cellulose as chosen from hydroxypropylmethyl cellulose, hydroxypropylmethyl cellulose phthalate, hydroxypropyl cellulose, methyl cellulose and a pharmaceutically acceptable alkali metal salt or alkaline earth metal salt of carboxymethyl cellulose, or pluran, carrageenan, polyvinylpyrrolidone or an alginic acid ester of polypropylene glycol, that the water-soluble high-molecular additive (ii) contained in the above-mentioned solid particles is present in said particles in a proportion of 0.5%~5% based on the weight of the Cefditoren pivoxil substance, that said particles fuse at a temperature of 120° C. or higher, but do not show any definite melting point, that the amorphous substance of Cefditoren pivoxil (i) contained in said particles does not show any peak of the angle of diffraction in a X-ray powder diffractometry chart of said particles but exhibits in its infrared absorption spectrum (as measured by pelleted potassium bromide method) a substantially broader peak of absorption at a wave number of 1750 cm$^{-1}$, as compared with the sharp peak of absorption exhibited by the orthorhombic crystalline substance of Cefditoren pivoxil at a wave number of 1750 cm$^{-1}$ in the infrared absorption spectrum, and that the amorphous substance of Cefditoren pivoxil (i) contained in said particles can be dissolved in an acidified water containing hydrochloric acid (pH 1.2) at a solubility of at least 4 mg/ml of Cefditoren pivoxil at 37° C. and has a crystallographical stability such that said amorphous Cefditoren pivoxil substance does not crystallize when stored at 40° C. for 4 months in a sealed container under dry conditions.

2. A composition as claimed in claim 1, which consists essentially of particles each formed of a homogeneous mixture of the crystallographically stable, amorphous and water-soluble substance of Cefditoren pivoxil with hydroxypropylmethyl cellulose, hydroxypropyl cellulose, methyl cellulose or polyvinylpyrrolidone blended as the water-soluble high-molecular additive which is present in an amount of 1%~3% based on the weight of Cefditoren pivoxil.

3. An orally administrable yellow-colored powdery composition consisting essentially of particles which each substantially comprise mixtures of a crystallographically stable, amorphous and water-soluble substance of Cefditoren pivoxil with water-soluble high-molecular additive or additives, and which particles have a uniform, internal texture within each particle, characterized in that the yellow-colored powdery composition consists essentially of the particles each substantially comprising a mixture of (i) the crystallographically stable, amorphous and water-soluble substance of Cefditoren pivoxil, namely 7-[(Z)-2-(2-aminothiazol-4-yl)-2-methoxyiminoacetamido]-3-[(Z)-2-(4-methylthiazol-5-yl) ethenyl]-3-cephem-4-carboxylic acid pivaloyloxymethyl ester, with (ii) a first, water-soluble high-molecular additive which is either such a pharmaceutically acceptable, water-solubilized derivative of cellulose as chosen from hydroxypropylmethyl cellulose, hydroxypropylmethyl cellulose phthalate, hydroxypropyl cellulose, methyl cellulose and a pharmaceutically acceptable alkali metal salt or alkaline earth metal salt of carboxymethyl cellulose, or pluran, carrageenan, polyvinylpyrrolidone or an alginic acid ester of polypropylene glycol, that the central portion or core portion of the respective particles which is lying under the surface layer of said respective particles is formed only from a homogeneous mixture of (i) the amorphous substance of Cefditoren pivoxil with (ii) the above-mentioned first, water-soluble high-molecular additive, but the surface layer of said particles is formed from a homogeneous mixture of (i) the amorphous substance of Cefditoren pivoxil with (ii)

the first water-soluble high-molecular additive and also with (iii) such a second, water-soluble high-molecular additive which is additionally incorporated, which is made of a substance different from the above-mentioned first water-soluble high-molecular additive present just in the central portion or core portion of said particles lying under said surface layer of the particle, and which second, water-soluble high-molecular additive is selected from hydroxypropylmethyl cellulose, hydroxypropyl cellulose, methyl cellulose and polyvinylpyrrolidone, that both the first water-soluble high-molecular additive (ii) and the second water-soluble high-molecular additive (iii) are present in a total proportion of them of 0.5%~5% based on the weight of the Cefditoren pivoxil substance contained in said particles, that said particles fuse at a temperature of 120° C. or higher, but do not show any definite melting point, that the amorphous substance of Cefditoren pivoxil (i) contained in said particles does not show any peak of the angle of diffraction in a powder X-ray diffractometry chart of said particles but exhibits in its infrared absorption spectrum (as measured by pelleted potassium bromide method) a substantially broader peak of absorption at a wave number of 1750 $cm^{-1}$, as compared with the sharp peak of absorption exhibited by the orthorhombic crystalline substance of Cefditoren pivoxil at a wave number of 1750 $cm^{-1}$ in the infrared absorption spectrum, and that the amorphous substance of Cefditoren pivoxil (i) contained in said particles can be dissolved in an acidified water containing hydrochloric acid (pH 1.2) at a solubility of at least 4 mg/ml of Cefditoren pivoxil at 37° C. and has a crystallographical stability such that said amorphous Cefditoren pivoxil substance does not crystallize when stored at 40° C. for 4 months in a sealed container under dry conditions.

4. A composition as claimed in claim 3, wherein the central portion or core portion of the respective particles which is lying under the surface layer of the respective particles is formed from a homogeneous mixture of the amorphous substance of Cefditoren pivoxil with hydroxypropylmethyl cellulose, but the surface layer of said particles is formed from a homogeneous mixture of the amorphous substance of Cefditoren pivoxil with hydroxypropylmethyl cellulose and also with hydroxypropyl cellulose or methyl cellulose.

5. A composition as claimed in claim 3, wherein the central portion or core portion of the respective particles which is lying under the surface layer of the respective particles is formed from a homogeneous mixture of the amorphous substance of Cefditoren pivoxil with hydroxypropyl cellulose, but the surface layer of said particles is formed from a homogeneous mixture of the amorphous substance of Cefditoren pivoxil with hydroxypropyl cellulose and also with hydroxypropylmethyl cellulose or methyl cellulose.

6. A composition as claimed in claim 3, wherein the central portion or core portion of the respective particles which is lying under the surface layer of the particles is formed from a homogeneous mixture of the amorphous substance of Cefditoren pivoxil with methyl cellulose, but the surface layer of said particles is formed from a homogeneous mixture of the amorphous substance of Cefditoren pivoxil with methyl cellulose and also with hydroxypropylmethyl cellulose or hydroxypropyl cellulose.

7. A composition as claimed in claim 3, wherein the central portion or core portion of the respective particles which is lying under the surface layer of the particles is formed from a homogeneous mixture of the amorphous substance of Cefditoren pivoxil with polyvinylpyrrolidone, but the surface layer of said particles is formed from a homogeneous mixture of the amorphous substance of Cefditoren pivoxil with polyvinylpyrrolidone and also with hydroxypropylmethyl cellulose or hydroxypropyl cellulose or methyl cellulose.

* * * * *